(12) United States Patent
Ikeda et al.

(10) Patent No.: US 6,926,884 B2
(45) Date of Patent: Aug. 9, 2005

(54) GPIB-LIPID BOND CONSTRUCT AND USE THEREOF

(75) Inventors: Yasuo Ikeda, 17-20, Koishikawa 3-chome, Bunkyo-ku, Tokyo 112-0002 (JP); Hiroshi Saito, Tokyo (JP); Hiromichi Mukai, Tokyo (JP); Yoshiyuki Mori, Tokyo (JP); Mitsuru Murata, Niiza (JP)

(73) Assignees: Mitsubishi Pharma Corporation, Osaka (JP); Yasuo Ikeda, Tokyo (JP)

( * ) Notice: Subject to any disclaimer, the term of this patent is extended or adjusted under 35 U.S.C. 154(b) by 0 days.

(21) Appl. No.: 10/220,610

(22) PCT Filed: Mar. 2, 2001

(86) PCT No.: PCT/JP01/01635

§ 371 (c)(1),
(2), (4) Date: Oct. 21, 2002

(87) PCT Pub. No.: WO01/64743

PCT Pub. Date: Sep. 7, 2001

(65) Prior Publication Data

US 2003/0113262 A1 Jun. 19, 2003

(30) Foreign Application Priority Data

Mar. 2, 2000 (JP) ........................................ 2000-057449

(51) Int. Cl.[7] ........................ A61K 38/14; A61K 47/34; A61K 49/00; A61K 51/08; C07K 14/475
(52) U.S. Cl. ...................... 424/1.69; 424/9.1; 424/9.34; 424/9.4; 424/9.6; 514/5; 514/6; 514/7; 514/8; 514/21; 530/381; 530/395; 530/408; 530/409; 530/410
(58) Field of Search ............................... 514/5, 6, 7, 8, 514/12, 21; 424/1.21, 1.69, 9.1, 9.321, 9.34, 9.341, 9.4, 9.51, 9.6; 530/352, 359, 381, 395, 408, 409, 410

(56) References Cited

U.S. PATENT DOCUMENTS

| | | | |
|---|---|---|---|
| 5,200,510 A | 4/1993 | Kumar et al. | 530/38.3 |
| 5,340,727 A | 8/1994 | Ruggeri et al. | 435/69.6 |
| 6,056,973 A | * 5/2000 | Allen et al. | 424/450 |

FOREIGN PATENT DOCUMENTS

| | | |
|---|---|---|
| EP | 894807 | 2/1999 |
| WO | 99/58694 | 11/1999 |

OTHER PUBLICATIONS

S. Zalipsky et al., "Poly(ethylene glycol)–grafted Liposomes with Oligopeptide or Oligosaccharide Ligands Appended to the Termini of the Polymer Chains", Bioconjugate Chemistry, 1997, vol. 8, No. 2, pp. 111 to 8, abstract.

S, Zalipsky et al., "Synthesis of an End–Group Functionalized Polyethylene Glycol–Lipid Conjugate for Preparation of Polymer–Grafted Liposomes", Bioconjugate Chemistry, 1993, vol. 4, No. 4, pp. 296 to 9, abstract, "Introduction".

M.S. Webb et al., "Comparison of Different Hydrophobic Anchors Conjugated to Poly(ethylene glycol) : effects on the Pharmacokinetics of Liposomal Vincristine", Biochimica et Biophysica ACTA, 1998, vol. 1372, No. 2, pp. 272 to 82, abstract; Table 1; Figs. 3 to 5.

* cited by examiner

Primary Examiner—Jeffrey Edwin Russel
(74) Attorney, Agent, or Firm—Wenderoth, Lind & Ponack L.L.P.

(57) ABSTRACT

The present invention provides a conjugate wherein GP (glycoprotein) Ib and a lipid are bonded via polyalkylene oxide. The present invention also provides a complex (GPIb lipid complex) containing this conjugate and a free lipid. The GPIb lipid complex is expected to have a potential for practical application in a wide range, as a platelet substitute, a pharmaceutical agent for the prophylaxis or treatment of angiopathy, vascular damage and thrombosis, a diagnostic for vWF deficiency and the like, a biological or medical reagent, a reagent for screening platelet aggregation suppressant or antithrombosis, and the like. The GPIb lipid complex of the present invention is also useful as a diagnostic for finding the location of vascular lesion or thrombus formation, or a therapeutic agent thereof. Moreover, the GPIb lipid complex of the present invention is also superior in retention property in blood, which enables continuous expression of a pharmacological action. The conjugate of the present invention is highly utilizable as an active ingredient of the GPIb lipid complex of the present invention.

24 Claims, No Drawings

GPIB-LIPID BOND CONSTRUCT AND USE THEREOF

This is a U.S. National Stage Application under 35 U.S.C. § 371 of PCT Application No. JP01/01635, filed Mar. 2, 2001.

TECHNICAL FIELD

The present invention relates to a conjugate of a GPIb and a lipid bonded via polyalkylene oxide (hereinafter to be also referred to as a GPIb-lipid conjugate), a lipid complex containing the conjugate and a free lipid, and use thereof.

BACKGROUND ART

Various glycoproteins (hereinafter to be referred to as GP) are present on the surface of a platelet membrane, and are involved in the expression of platelet functions. Of such platelet membrane glycoproteins, GPIb, GPIIb, GPIIIa, GPIIIb, GPIV, GPIX and the like are known. Of these, GPIb functions as a receptor of the von Willebrand Factor (hereinafter to be referred to as vWF). GPIb is a heterodimer having a molecular weight of 160,000, wherein α chain and β chain are bonded via a disulfide bond (Proc. Natl. Acad. Sci. USA, Vol. 84, pp. 5615–5619, 1987, Hematology & Oncology, Vol. 31, No. 1, pp. 5–10, 1995 and the like).

When vascular damages are caused, platelets quickly adhere to the vascular lesion and form a platelet thrombus by aggregation and the like. In forming the platelet thrombus, vWF plays an important role as an adhesive protein. It is considered that GPIb binds with vWF as its receptor and activates or promotes adhesion and aggregation of platelets via vWF at said vascular lesion. In addition, the binding of vWF and GPIb functions to stop bleeding at the vascular lesion but also forms a pathologic thrombus. Thus, effective use of GPIb for the examination and diagnosis of vascular lesion, detection of pathologic thrombus, and treatment thereof is expected.

Nevertheless, the use of isolated GPIb has not proved successful in artificial expression of the physiological activity as mentioned above. In other words, some idea in the aspect of formulation of pharmaceutical preparations is needed to practically use GPIb as a pharmaceutical agent or reagent.

The present inventors first found earlier that the physiological activity of GPIb could be expressed by preparing a lipid complex containing a conjugate of GPIb and a particular lipid, and a general lipid (WO97/29128, JP-A-9-208599, U.S. Pat. No. 6,177,059, EP-894807-A).

DISCLOSURE OF THE INVENTION

In view of the above-mentioned situation, the present inventors have further studied, and as a result, found that a GPIb-lipid conjugate showing superior retention property in blood can be prepared by introducing polyalkylene oxide (hereinafter to be referred to as PAO) between GPIb and the lipid, and intensively studied further to complete the present invention.

Accordingly, the present invention relates to (1) a conjugate comprising GPIb and a lipid that are bonded via PAO (hereinafter to be also referred to as a GPIb-lipid conjugate), (2) the conjugate of (1) above, wherein the GPIb is a GPIb itself, a GPIb fragment, a GPIb α chain or a GPIb α chain fragment, (3) the conjugate of (1) above, wherein the GPIb is an analog, a mutant, a modified compound, a derivative or a sugar chain adduct, having a von Willebrand Factor-binding capability almost of the same level as GPIb, (4) the conjugate of (1) above, wherein the GPIb lacks a transmembrane site, (5) the conjugate of (1) above wherein the lipid has a functional group, (6) the conjugate of (5) above, wherein the lipid having a functional group is a phospholipid, a glycolipid, a fatty acid, a glyceride, a cholesterol or an amphipathic lipid, (7) the conjugate of (5) above, wherein the functional group is an amino group, a carboxyl group, a thiol group or an aldehyde group, (8) the conjugate of (1) above, wherein the PAO is polyethylene glycol, polypropylene glycol, or glycol obtained by copolymerizing ethylene oxide and propylene oxide, (9) the conjugate of (1) above, wherein the PAO has a number average molecular weight of 100–100000,

(10) the conjugate of (5) above, wherein the GPIb and the PAO, and the PAO and the lipid having a functional group are respectively bonded chemically by a crosslinking agent,

(11) the conjugate of (5) above, wherein a molar ratio of GPIb:PAO is 1:1–1:20 and a molar ratio of the PAO:lipid having a functional group is 1:1,

(12) a complex comprising a GPIb-lipid conjugate and a free lipid (hereinafter to be also referred to as a GPIb lipid complex),

(13) the complex of (12) above, which is in the form of a liposome,

(14) the complex of (12) above, wherein the free lipid is a phospholipid, a glycolipid, a cholesterol, a fatty acid or a derivative thereof,

(15) the complex of (12) above, wherein a molar ratio of the GPIb:free lipid is 1:10–1:1000,

(16) the complex of (12) above, wherein the complex is aggregatable in the presence of ristocetin,

(17) the complex of (12) above, wherein the conjugate comprising GPIb and the lipid bonded via PAO is prepared and then the complex of said conjugate and a free lipid is prepared,

(18) a pharmaceutical composition containing the complex of (12) above,

(19) the pharmaceutical composition of (18) above, which is a platelet substitute,

(20) the pharmaceutical composition of (18) above, which is an agent for the prophylaxis or treatment of a vascular disorder, a vascular damage or thrombosis,

(21) a pharmaceutical agent for examination or diagnosis, which comprises, as an active ingredient, a labeling substance and the complex of (12) above,

(22) the pharmaceutical agent of (21) above, wherein the labeling substance is a radioisotope, a paramagnetic metal for MRI, an iodide compound for X ray imaging, a fluorescent substance or a pigment,

(23) a drug-containing composition comprising a drug and the complex of (12) above as active ingredients, and

(24) the drug-containing composition of (23) above, wherein the drug is a hemostatic agent, a vasoconstrictor, an antiinflammatory agent, a thrombolytic agent, an anti-blood coagulator or an anti-platelet agent. The present invention is described in detail in the following.

(I) Conjugate Consisting of GPIb-PAO-Lipid (GPIb-Lipid Conjugate)

The GPIb-lipid conjugate of the present invention is a conjugate wherein (A) GPIb and (B) a lipid are bonded via (C) PAO.

(A) GPIb

The GPIb to be used in the present invention may be any as long as it has a binding capability with vWF, and includes natural GPIb itself, and those obtained by subjecting one or plural amino acids of the amino acid sequence thereof to an optional mutation, such as deletion, substitution, addition and modification, to the degree that the object of the present invention can be still achieved, that are exemplified by substitute, analog, mutant, modified compound, derivative, sugar chain adduct and the like of natural GPIb. Specific examples include GPIb fragments such as α chain [His(1)-Leu(610)] of GPIb, a fragment of a vWF binding region of the α chain (hereinafter to be also referred to as a GPIb α chain fragment) and the like, GPIb fragments wherein transmembrane site has been deleted, and the like. In the present invention, GPIb fragments without the transmembrane site are more preferably used.

More specific GPIb α chain fragments include His(1)-Cys(485), His(1)-Pro(340), His(1)-Thr(304), His(1)-Ala(302), His(1)-Arg(293) [JP-A-1-221394, EP-317278-A], Ala(165)-Leu(184), Gln(180)-Phe(199), His(195)-Leu(214), Asn(210)-Val(229), Glu(225)-Ala(244) and Thr(240)-Tyr(259) [JP-A-1-100196], Asn(61)-Thr(75), Gln(71)-Ser(85), Thr(81)-Leu(95), Gln(97)-Arg(111), Leu(136)-Leu(150), Asn(210)-Ala(224), Gln(221)-Asp(235) and Ser(241)-Asp(255) [Japanese Patent Application under PCT laid-open under kohyo No. 5-503708, WO91/09614] and the like. Examples of the substitute include a GPIb α chain fragment consisting of His(1)-Ala(302), wherein Gly(233) or Met(239) is substituted by Val, and the like [WO93/16712]. These GPIb α chain fragments all lack transmembrane site. The transmembrane site in the GPIb α chain is Leu(486)-Gly(514) (Proc. Natl. Acad. Sci. USA, Vol. 84, pp. 5615–5619, 1987).

The GPIb can be prepared by any method and a method comprising extraction and isolation from platelet membrane, a method using cell culture and a production method using genetic engineering are exemplified.

(B) Lipid

The lipid that is bonded to GPIb via PAO has a functional group directly or indirectly bondable to PAO. Such functional group is exemplified by amino group ($NH_2$), carboxyl group (COOH), thiol group (SH), aldehyde group (CHO) and the like. As long as the functional group can form a direct or indirect bond with PAO, it is not limited to those exemplified.

The kind of the lipid is exemplified by phospholipid, glycolipid, fatty acid, glyceride, cholesterols and the like, with preference given to amphipathic ones.

The lipid is exemplified by phosphatidylethanolamine (hereinafter to be referred to as PE) and phosphatidylthioethanol (e.g., 1,2-dioleoyl-sn-glycero-3-phosphatidylthioethanol) for phospholipid. As the glycolipid, for example, ceramide, cerebroside, sphingosine, sulfatide, gangliosides and glyceroglycolipids (e.g., galactosyldiacylglycerol) and the like are mentioned. The fatty acid is exemplified by saturated or unsaturated fatty acid having 12 to 18 carbon atoms, which may be, for example, palmitic acid, oleic acid or lauric acid. As the glyceride, for example, monoglyceride, diglyceride, triglyceride and the like are mentioned. The cholesterols include cholesterol, cholesterol ester and allocholesterol. The functional group in these lipids may be in the form of an acid halide, an acid anhydride or an active ester, to enhance the reactivity with PAO and the crosslinking agents to be mentioned later.

For an indirect bonding of a lipid and PAO, one obtained by reacting a crosslinking agent (i.e., spacer or linker) with the functional group of a lipid in advance can be also used. Examples of such crosslinking agent include dicarboxylic acid, aminocarboxylic acid, bismaleimide compound, bishalocarbonyl compound, halocarbonylmaleimide compound, dithiomaleimide, dithiocarboxylic acid, maleimidocarboxylic acid and the like. These crosslinking agents preferably have 2 to 10 carbon atoms. These crosslinking agents and the functional group of a lipid are reacted according to a conventional method.

The phospholipid formed by reacting said crosslinking agent with the functional group is exemplified by PE-N-carbonyl amine (e.g., PE-N-caproyl amine, PE-N-dodecanyl amine, PE-N-glutaryl amine and the like), PE-N-carbonyl (e.g., PE-N-succinyl, PE-N-glutaryl (NGPE), PE-N-dodecanyl (NDPE) and the like), PE-N-dithioacylate (e.g., PE-N-3-(2-pyridyldithio)-propionate), PE-N-maleimidoacylate (e.g., PE-N-4-(p-maleimidophenyl) butyrate and the like), PE-N-biotinyl and the like.

(C) PAO (Polyalkylene Oxide)

PAO is present between (A) GPIb and (B) a lipid and binds the two. The PAO is the same as polyalkylene glycol and exemplified by polyethylene glycol (PEG), polypropylene glycol, glycol obtained by copolymerization of ethylene oxide and propylene oxide, and the like. PAO has a high number average molecular weight of about 100–100,000, preferably about 1,000–10,000.

As the PAO, moreover, one obtained by reacting one or both of the termini of PAO with a crosslinking agent (i.e., spacer, linker) in advance can be also used. Examples of the crosslinking agent include dicarboxylic acid, aminocarboxylic acid, bismaleimide compound, bishalocarbonyl compound, halocarbonylmaleimide compound, dithiomaleimide, dithiocarboxylic acid, maleimidocarboxylic acid and the like. These crosslinking agents and PAO are reacted according to a conventional method.

(D) Preparation of GPIb-Lipid Conjugate

The bond between GPIb and PAO, and the bond between PAO and a lipid having a functional group are directly or indirectly formed chemically, i.e., via or not via a group derived from a crosslinking agent. In the present invention, an indirect bond is preferred. The molar mixing ratio of GPIb:PAO or a lipid having a functional group is about 1:1–1:20, preferably about 1:1–1:10.

When the chemical bond between GPIb or a lipid having a functional group and PAO cannot be formed directly, a method comprising reacting the functional group of a lipid or PAO with the above-mentioned crosslinking agent may be employed, or a known condensing agent, an activating agent that activates the functional group in the lipid, a divalent crosslinking agent and the like may be used. Examples of the condensing agent and the activating agent include carbodiimides (e.g., N,N'-dicyclohexylcarbodiimide, 1-ethyl-3-(3-dimethylaminopropyl)carbodiimide (EDC) and the like), succinimides (e.g., N-hydroxysuccinimide, N-hydroxysulfosuccinimide (NHSS) and the like), a compound used for exchange reaction of thiol group (e.g., 5,5'-dithiobis(2-nitrobenzoic acid), 2,2'-dithiobispyridine and the like), and the like.

The divalent crosslinking agent may be a crosslinking agent having the same or different reactivity. Examples of the crosslinking agent having the same reactivity include dimethyl adipimidate, disuccinimidyl suberate and the like, and examples of the crosslinking agent having different reactivity include succinimidyl-3-(2-pyridyldithio) propionate, N-(6-maleimidocaproyloxy)succinimide, N-succinimidyl-6-maleimidohexanoate and the like.

As direct bond of GPIb or lipid and PAO, —COO— [e.g., obtained by ester bonding of carboxyl group of GPIb or lipid (e.g., fatty acid) and hydroxyl group of PAO], —O— (e.g., obtained by ether bonding of hydroxyl group of GPIb or lipid and hydroxyl group of PAO), —CONH— (e.g., obtained by amide bonding of carboxyl group of GPIb or lipid and amino group introduced into PAO), —CH=N— (e.g., obtained by Schiff bonding of aldehyde group on sugar chain of GPIb or aldehyde group introduced into lipid and amino group introduced into PAO), —CH$_2$NH— (obtained by further reduction of Schiff bond), —NH— and the like are mentioned.

Of the specific methods for indirectly bonding GPIb or lipid and PAO, the mode of bonding of the crosslinking agent (inclusive of divalent crosslinking agent, hereinafter the same) and PAO is exemplified by —COO—, —O—, —CONH—, —CH=N—, —CH$_2$NH—, —NH— and the like, like those mentioned above. As the mode of bonding of GPIb or lipid and the crosslinking agent, there are mentioned, besides those similar to the above-mentioned, —S—S— [obtained by disulfide bonding of thiol group of GPIb or lipid (e.g., phosphatidylthioethanol) and dithio moiety of crosslinking agent such as dithiomaleimide, dithiocarbonyl compound and the like], —S— (obtained by bonding thiol group of GPIb or lipid and crosslinking agent such as maleimide compound, halocarbonyl compound and the like, by reductive alkylation), —NH— (e.g., obtained by reacting amino group of GPIb or lipid (e.g., PE) and maleimide moiety of crosslinking agent, such as maleimidocarboxylic acid and the like), —CO— and the like.

The GPIb-lipid conjugate may be prepared in the presence of a surfactant. The surfactant is not particularly limited as long as it solubilizes lipid. The use of a nonionic surfactant is preferable, so that the structure of GPIb will not be influenced. In particular, a nonionic surfactant having a high critical micelle concentration (CMC), such as a CMC of not less than 1 mM, is preferable. Examples thereof include octyl glucoside (e.g., n-octyl-β-D-glucoside), octyl thioglucoside (e.g., n-octyl-β-D-thioglucoside), 3-[(3-cholamidopropyl)-dimethylammonio]propanesulfate (CHAPS) and N,N-bis(3-D-gluconamidopropyl) deoxycholamide (deoxy-BIGCHAP). The mixing ratio of lipid:surfactant is preferably about 0.01:1–0.1:1 by mole.

(E) Activated Lipid Consisting of Reactive Substituent-PAO-Lipid (Hereinafter to be also Referred to Simply as an Activated Lipid)

As an intermediate for synthesizing a conjugate (GPIb-lipid conjugate) consisting of GPIb-PAO-lipid, an activated lipid consisting of reactive substituent-PAO-lipid can be used. As used herein, by the "activated lipid" is meant a bonded product of PAO and lipid having a reactive substituent on the terminal of PAO. PAO and the lipid are directly or indirectly bonded chemically via or not via a group derived from a crosslinking agent. The reactive substituent is subject to no particular limitation as long as it has an action of activating a bond with a protein. For example, it can be obtained by reacting succinimide, maleimide and the like with the terminal of PAO. The mode of the bond between the reactive substituent and PAO, and PAO and a lipid in the activated lipid is as shown under the above-mentioned (D) Preparation of GPIb-lipid conjugate.

By directly or indirectly bonding activated lipid and GPIb chemically, i.e., via or not via a crosslinking agent, a GPIb-lipid conjugate can be obtained.

As the activated lipid, the following compounds are specifically exemplified. These activated lipids are known and can be produced according to a known method. Alternatively, a commercially available products can be used.

DSPE-34HCSI: distearoylphosphatidyl-N-(succinimidylsuccinyl-polyoxyethylene-succinyl) ethanolamine. The number average molecular weight of PEG is 3400.

DSPE-20HMAL: distearoylphosphatidyl-N-(maleimidopropionylamino-polyoxyethylene-oxycarbonyl)-ethanolamine. The number average molecular weight of PEG is 2000.

(F) Property of GPIb-Lipid Conjugate

The GPIb-lipid conjugate of the present invention comprises GPIb and PAO or lipid in a constituting molar ratio of about 1:1–1:20. The constituting molar ratio of PAO and lipid is 1:1.

(II) Complex of GPIb-Lipid Conjugate and Free Lipid (GPIb Lipid Complex)

The complex of the present invention containing the above-mentioned GPIb-lipid conjugate and free lipid can take the form of a liposome, micell or lipid emulsion, with preference given to a liposome. As an example of the complex of the present invention, a GPIb lipid complex in the form of a liposome is explained. The explanation of the following GPIb lipid complex applies to other forms besides liposome.

(A) Free Lipid

The lipid to be used here is free of limitation as long as it can take the form of a lipid complex, such as a liposome, and may be used alone or in combination with other lipid. Examples of such lipid include phospholipid, glycolipid, cholesterol, fatty acid and derivatives thereof. The free lipid to be used in the present invention for forming the complex may be any non-toxic lipid as long as it is physiologically acceptable and metabolizable. Note that a free lipid means a lipid other than a lipid constituting the GPIb-lipid conjugate, and may be homologous or heterologous with the lipid constituting the GPIb-lipid conjugate.

Examples of the phospholipid include phosphatidylcholine (hereinafter to be referred to as PC), phosphatidylserine, phosphatidic acid, phosphatidylglycerol, phosphatidylinositol, sphingomyelin, dicetyl phosphate, cardiolipin, lysophosphatidylcholine and the like. These lipids may be extracted and purified from a natural material such as soybean oil or egg yolk, or prepared by hydrogenation thereof to saturate the constituent fatty acid (hydrogenated phospholipid), or obtained by substituting the constituent fatty acid with specific fatty acid, such as palmitic acid and myristic acid (e.g., diacylphosphatidylcholine, diacylphosphatidyl glycerol and the like). Specific examples thereof include purified egg yolk lecithin, hydrogenated purified soybean lecithin, egg yolk-originated phosphatidylcholine, dipalmitoylphosphatidylcholine, dipalmitoylphosphatidyl glycerol, distearylphosphatidylcholine, dimyristylphosphatidylcholine and the like.

Glycolipid may be, for example, ceramide, cerebroside, sphingosine, sulfatide, gangliosides or glyceroglycolipids.

The cholesterols include cholesterol, cholesterol ester and allocholesterol.

The fatty acid is exemplified by oleic acid, lauric acid, myristic acid, palmitic acid and stearic acid. Examples of the lipid derivative include polyoxyethylene derivative having phosphatidyl ethanolamine and fatty acid, and polysaccharide derivative having fatty acid and cholesterol. Specifically, it may be distearyl-N-(monomethoxypolyethylene glycol succinyl)-phosphatidyl ethanolamine, polyoxyethylene palmitate, N-[2-(stearoylcarboxy-amino)ethyl]carbamoyl methyl mannan or N-[2-(cholesterylcarboxy-amino)ethyl] carbamoylmethylpluran.

(B) Formation of Complex

As the mixing ratio of GPIb-lipid conjugate:free lipid, the molar mixing ratio of GPIb:free lipid is about 1:10–1:1000, preferably about 1:50–1:200.

A GPIb lipid complex (e.g., liposome) can be prepared by, for example, surfactant removal method, hydrate method, ultrasonication, reversed phase evaporation method, freeze-thaw method, ethanol injection method, extrusion method or high pressure emulsification. The surfactant removal method is generally gel filtration, dialysis or ultrafiltration. In the present invention, a method comprising forming a complex after bonding GPIb and a lipid via PAO, or forming a lipid complex after preparation of a GPIb-lipid conjugate, is more preferable. It is also possible to prepare a GPIb lipid complex by adding GPIb after preparation of a lipid complex (e.g., liposome) consisting of the lipid of (I)(B) and the free lipid of (II)(A), thereby to bond the lipid of (I)(B) and GPIb via PAO. The GPIb lipid complex can be isolated and purified by a method known per se, such as centrifugation and gel filtration.

The production method of the GPIb lipid complex is exemplified in the following.

(i) Method for Forming a GPIb Lipid Complex after Preparation of a GPIb-Lipid Conjugate A lipid [(I)(B)] is solubilized with a surfactant and bonded with PAO to give a bonded product. This bonded product, GPIb and a free lipid [(II)(A)] are mixed in a suitable aqueous solvent to allow bonding of GPIb and the lipid [(I)(B)] via PAO, and then the surfactant is removed to form a GPIb lipid complex. Alternatively, a bonded product of the lipid [(I)(B)] and PAO and GPIb are mixed in the presence of a surfactant to prepare a GPIb-lipid conjugate, a free lipid [(II)(A)] is mixed and the surfactant is removed, thereby to give a GPIb lipid complex. The unreacted GPIb, lipid [(I)(B)], free lipid [(II)(A)] and the like may be separated and removed to give a purified product. The surfactant is the same as those mentioned above. The mixing ratio (free lipid [(II)(A)]:surfactant) is about 0.001:1–0.1:1 (molar ratio).

(ii) Method for Bonding GPIb After Preparation of a Lipid Complex (e.g., Liposome) to Give GPIb Lipid Complex The bonded product of lipid [(I)(B)] and PAO, and free lipid [(II)(A)] are dissolved and mixed in an organic solvent such as chloroform and ethanol, and the organic solvent is removed to give a thin lipid membrane. A suitable aqueous solvent is added and the mixture is treated by a known method, such as shaking and stirring, to give a lipid complex. GPIb is added to form a bond of GPIb and the lipid via PAO, whereby a GPIb lipid complex is formed. The unreacted GPIb, lipid and the like may be separated and removed to give a purified product.

For this method, a free lipid [(II)(A)] that does not react/bind with GPIb is used. Specially, phosphatidylcholine, lysophosphatidylcholine and the like are used.

The proportion of GPIb to free lipid [(II)(A)] in the obtained GPIb lipid complex is 0.01–10 parts by weight, preferably 0.1–5 parts by weight, per part by weight of the free lipid [(II)(A)].

The obtained GPIb lipid complex has a particle size of about 50–500 nm, preferably about 100–400 nm. The number of GPIb molecules per particle is 100–10000, preferably 250–3000 and the surface density of GPIb is $10^{10}$–$10^{13}$, preferably $10^{11}$–$10^{12}$.

The GPIb lipid complex (e.g., liposome) has a structure of multilamella vesicle (MLV), small unilamella vesicle, large unilamella vesicle and the like. It may be coated with a hydrophilic polymer such as polyethylene glycol (PEG), pluronic (registered trademark) (polyoxyethylene polyoxypropylene block copolymer) and the like.

Where necessary, the obtained GPIb lipid complex is washed with a physiologically acceptable aqueous solution, sterilized by filtration, dispensed and formulated into a liquid, pellet or suspension preparation.

The complex can be processed by a method known to be usable for the preparation of pharmaceutical products. The above-mentioned preparations may be provided as lyophilized preparations upon freezing a liquid preparation and drying same under reduced pressure. For lyophilization, monosaccharides (e.g., glucose), disaccharides (e.g., sucrose) and the like may be added.

The preparations of GPIb lipid complex may contain, as a stabilizer, a polymer selected from albumin, dextran, vinyl polymer, gelatin and hydroxylethyl starch.

The polymer may be incorporated into the gaps present in said lipid complex together with a drug. Alternatively, the polymer may be added to or contained in said lipid complex preparation containing a drug. This means that the polymer may be added or incorporated outside the liposome. It is needless to say that it can be incorporated both inside and outside the lipid complex.

The stabilizer is added in an amount of 0.5–10 parts by weight, preferably 1–5 parts by weight, per part by weight of the free lipid [(II)(A)].

(III) Use of GPIb Lipid Complex as Pharmaceutical

The GPIb lipid complex of the present invention can be embodied as a diagnostic of the location of vascular lesion or thrombus formation, von Willebrand Factor deficiency and the like by adding a labeling substance (so-called a marker). Examples of such labeling substance include RI (radioisotope), paramagnetic metal for MRI, iodide compound for X ray imaging, fluorescent substance and pigment.

RI is exemplified by $^3$H, $^{14}$C, $^{99m}$Tc, $^{123}$I, $^{125}$I, $^{131}$I, $^{87m}$Sr, $^{113m}$In, $^{197}$Hg and the like. The paramagnetic metal for MRI is exemplified by divalent ion and trivalent ion of a paramagnetic metal of chromium (Cr), gadrinium (Gd), manganese (Mn), iron (Fe), cobalt (Co), nickel (Ni), praseodymium (Pr), neodium (Nd), samarium (Sm), ytterbium (Yb), terbium (Tb), dysprosium (Dy), hormium (Ho), erbium (Er), copper (Cu) and the like, with preference given to divalent ion and trivalent ion of gadrinium, terbium, dysprosium, hormium, erbium and iron.

The iodide compound for X ray imaging may be a known compound for X ray imaging. Examples thereof include adipiodone, amidotrizoic acid, iotalamic acid, iopanoic acid, iobenzamic acid, iopodate, tyropanoic acid, iopydol, iopydone, propyliodone, iodamide and salts thereof (e.g., sodium salt and meglumine salt). The fluorescent substance may be, for example, fluorescein isothiocyanate (FITC), carboxyfluorescein (CF) and the like.

These labeling substances can be encapsulated in a lipid complex (e.g., liposome) by a known method. For example, it can be enclosed in a lipid complex in the form of a salt or after chelating with a chelating agent such as ethylenediaminetetraacetic acid (EDTA) and diethylenetriaminepentaacetic acid (DTPA). In the case of $^{99m}$Tc, for example, sodium pertechnetate, technetium polyphosphate or $^{99m}$Tc DTPA can be used.

The pharmaceutical agent for examination or diagnosis, which contains a labeling substance and the GPIb lipid complex of the present invention may be a GPIb lipid complex of the present invention, which is prepared according to a method mentioned above and using GPIb labeled with a labeling substance (e.g., RI).

The GPIb lipid complex of the present invention is cumulative at the vascular lesion and thus, may be formed into a composition containing a drug (drug vehicle). The drug to be contained is free of any particular limitation as long as it proves physiologically and pharmacologically effective upon accumulation thereof at the vascular lesion, and may be, for example, hemostatic agent, vasoconstrictor, antiinflammatory agent, thrombolytic agent, anti-blood coagulator, anti-platelet agent and the like.

The hemostatic agent is exemplified by carbazochrome, blood coagulation factor (FVIII, FIX), thrombin, antiplasmin agent (e.g., ε-aminocaproic acid and tranexamic acid), protamine sulfate, etamsylate, phytonadione and conjugated estrogen (e.g., sodium estrone sulfate and sodium equilin sulfate) and the like.

The vasoconstrictor is exemplified by noradrenaline, norfenefrine, phenylephrine, metaraminol, methoxamine, prostaglandin $F_1$ α, prostaglandin $F_2$ α, thromboxane $A_2$ and the like. The antiinflammatory agent is exemplified by steroidal antiinflammatory agent (e.g., dexamethasone, hydrocortisone, prednisolone, betamethasone, triamcinolone, methylprednisolone and the like), non-steroidal antiinflammatory agent (e.g., indometacin, acemetacin, flurbiprofen, aspirin, ibuprofen, flufenamic acid, ketoprofen, and the like) and the like.

The thrombolytic agent is exemplified by plasmin, tissue plasminogen activator, urokinase, precursors thereof and derivatives thereof. The anti-blood coagulator is exemplified by acidic mucopolysaccharide (e.g., heparin), coumarin anti-blood coagulator, natural extract (e.g., hirudine) and derivatives thereof, physiologically active substances (e.g., thrombomodulin, active protein C, and the like) and the like. The anti-platelet agent is exemplified by aspirin, ticlopidine, cilostazol, prostacyclin and the like. These drugs can be encapsulated in a lipid complex by a known method.

The inventive GPIb lipid complex is administered in an amount of about 0.001–1000mg as GPIb per day. The dose can be appropriately changed depending on the sex, age and symptoms of patients.

The GPIb lipid complex is more preferably administered parenterally. To be specific, it is administered by intravascular (intraarterial or intravenous) injection, intravenous drip, subcutaneous administration, local administration, intramuscular administration and the like.

The pharmaceutical composition containing the inventive GPIb lipid complex is useful as a platelet substitute, a pharmaceutical product for the prophylaxis or treatment of angiopathy, vascular damages and thrombosis, a diagnostic for vWF deficiency and the like, a biological or medical reagent, a reagent for screening platelet aggregation suppressant or antithrombosis, and the like. It is also useful for a diagnostic for finding the location of vascular lesion or thrombus formation, or a therapeutic agent thereof.

EXAMPLES

The present invention is explained in more detail in the following by way of Examples and Experimental Examples, which are not to be construed as limitative. The GPIb subjected to the Examples and Experimental Examples of the present invention was a GPIb α chain fragment [His(1)-Arg(293), molecular weight 45000, JP-A-9-208599] produced by genetic engineering using a CHO cell.

Example 1

To physiological saline (100 μL) containing GPIb (100 mg/mL) were added egg yolk phosphatidylcholine (EPC) (221 mg), cholesterol (45.4 mg) and octyl glucoside (OG) (2.33 g), dissolved in water for injection (1.5 mL). The amount of EPC corresponded to a 100-fold molar ratio of GPIb. Then, DSPE-34HCSI (purchased from NOF Corporation) dissolved in HEPES buffer (pH 8.0) containing 0.1% OG was added. The amount of DSPE-34HCSI added was a 10-fold molar amount of GPIb. After reaction at 4° C. for 16 hr, OG was removed by gel filtration (carrier was Sephadex G-75, Pharmacia Biotech) to give a liposome. GPIb liposome was recovered by centrifugal separation by CsCl density gradient method. The conditions therefor were as follows. CsCl was dissolved in a sample (1–1.5 mL) to a concentration of 35%, and 0.5 mL of 25% CsCl and 0.1 mL of physiological saline were layered thereon and treated at 214000×g for 10 min. The liposome-containing fraction was recovered and dialyzed overnight against a dialysis membrane (molecular weight of fraction 10,000 dalton, Slide-A-Lyzer 10K, Pierce Biotechnology, Inc.) using physiological saline. The prepared GPIb liposome had a PC concentration of 0.61 mg/mL, a GPIb concentration of 0.24 mg/mL, and an average particle size of 0.25 μm.

Example 2

To 1,3,4,6-tetrachloro-3α,6α-diphenylglycouril (200 μg) were added $Na^{125}I$ solution (448 MBq/mL, 30 μL), and then physiological saline (100 μL) containing GPIb (100 mg/mL), and the mixture was reacted at room temperature for 10 min. 25 mM NaI (100 μL) was added and the mixture was subjected to gel filtration (MicroSpin G-25, Pharmacia Biotech) and ultrafiltration (Ultrafree-MC10K, Millipore Corporation) to give iodine-labeled GPIb ($^{125}I$-GPIb).

The operation followed that of Example 1 except the above-mentioned $^{125}I$-GPIb was used instead of GPIb. The prepared GPIb liposome had a PC concentration of 3.54 mg/mL, a GPIb concentration of 1.00 mg/mL, an average particle size of 0.33 μm, and radioactivity of $9.3 \times 10^7$ cpm/mL.

Experimental Example 1

The aggregation capability of the GPIb liposome was confirmed. The GPIb liposome prepared in Example 1 was adjusted to a PC concentration of 0.2 mg/mL. To the solution (200 μL) was added 2 mg/mL of a vWF solution (25 μL) and the mixture was incubated and stirred at 37° C. After 2 min, 15 mg/mL of a ristocetin solution (25 μL) was mixed. The aggregate was measured for the total of 15 min from immediately before incubation using an aggregometer (AG-10, Kowa Company, Ltd.). The total of the values of aggregate number multiplied by scattering intensity was calculated and used as an index of the degree of aggregate formation. The results are shown in Table 1.

A similar experiment was performed using, as a control, a GPIb liposome (described in Example 1 of JP-A-9-208599) without PEG. The results are shown in Table 2.

TABLE 1

| | Degree of aggregate formation ($\times 10^4$) | | |
| --- | --- | --- | --- |
| Test time | Small aggregate | Medium aggregate | Large aggregate |
| Immediately before | 0 | 0 | 0 |
| 5 min later | 3.1 | 4.0 | 9.5 |
| 10 min later | 2.0 | 2.8 | 10.3 |
| 15 min later | 1.3 | 1.3 | 8.0 |

TABLE 2

| Test time | Degree of aggregate formation ($\times 10^4$) | | |
|---|---|---|---|
| | Small aggregate | Medium aggregate | Large aggregate |
| Immediately before | 0 | 0 | 0 |
| 5 min later | 0.4 | 0.2 | 0 |
| 10 min later | 1.7 | 1.7 | 3.0 |
| 15 min later | 1.8 | 2.0 | 7.8 |

The GPIb liposome of the present invention specifically reacted with vWF in the presence of ristocetin and formed an aggregate. This has demonstrated that the GPIb liposome is useful as a platelet substitute. In addition, the GPIb liposome of the present invention has been clarified to have improved the aggregation capability as compared to the control.

Experimental Example 2

The hemodynamics of the GPIb liposome was confirmed. The iodine labeled GPIb liposome prepared in Example 2 was administered to Hartley guinea pigs (n=3) at the dose of 1 mg/kg body weight in GPIb into the femoral vein. The blood was drawn from the orbital with the lapse of time for 60 min after the administration and the radioactivity of blood (100 μL) was counted on a gamma counter (1 min). A similar experiment was performed using, as a control, a GPIb liposome (described in Example 1 of JP-A-9-208599) without PEG. The results are shown in Table 3.

TABLE 3

| Time after administration | blood concentration (%: relative to dose) | |
|---|---|---|
| | Example 2 | control |
| 2 min later | 53 | 18 |
| 5 min later | 27 | 3 |
| 10 min later | 16 | 2 |
| 30 min later | 9 | 6 |
| 60 min later | 8 | 7 |

The GPIb liposome of the present invention has been clarified to have improved the retention property in blood as compared to the control.

INDUSTRIAL APPLICABILITY

The GPIb lipid complex of the present invention can bind with vWF and form an aggregate. Thus, it is expected to have a potential for practical use in a wide range as a platelet substitute, a pharmaceutical agent for the prophylaxis or treatment of angiopathy, vascular damage and thrombosis, a diagnostic for vWF deficiency and the like, a biological or medical reagent, a reagent for screening platelet aggregation suppressant or antithrombosis, and the like. The GPIb lipid complex of the present invention is also useful as a diagnostic for finding the location of vascular lesion or thrombus formation, or a therapeutic agent thereof, since it specifically accumulates at vascular lesions. Moreover, the GPIb lipid complex of the present invention is also superior in retention property in blood, which enables continuous expression of a pharmacological action.

The GPIb-lipid conjugate of the present invention is highly utilizable as an active ingredient of the GPIb lipid complex of the present invention.

This application is based on application No. 2000-57449 filed in Japan, the contents of which are incorporated hereinto by reference.

What is claimed is:

1. A conjugate comprising GPIb and a lipid that are bonded via polyalkylene oxide (PAO).
2. The conjugate of claim 1, wherein the GPIb is a GPIb itself, a GPIb fragment, a GPIb α chain or a GPIb α chain fragment.
3. The conjugate of claim 1, wherein the GPIb is an analog, a mutant, a modified compound, a derivative or a sugar chain adduct, having a von Willebrand Factor-binding capability almost of the same level as GPIb.
4. The conjugate of claim 1, wherein the GPIb lacks a transmembrane site.
5. The conjugate of claim 1, wherein the lipid has a functional group.
6. The conjugate of claim 5, wherein the lipid having a functional group is a phospholipid, a glycolipid, a fatty acid, a glyceride, a cholesterol or an amphipathic lipid.
7. The conjugate of claim 5, wherein the functional group is an amino group, a carboxyl group, a thiol group or an aldehyde group.
8. The conjugate of claim 1, wherein the PAO is polyethylene glycol, polypropylene glycol, or glycol obtained by copolymerizing ethylene oxide and propylene oxide.
9. The conjugate of claim 1, wherein the PAO has a number average molecular weight of 100–100000.
10. The conjugate of claim 5, wherein the GPIb and the PAO, and the PAO and the lipid having a functional group are respectively bonded chemically by a crosslinking agent.
11. The conjugate of claim 5, wherein a molar ratio of GPIb:PAO is 1:1–1:20 and a molar ratio of the PAO:lipid having a functional group is 1:1.
12. A complex comprising the conjugate of claim 1 and a free lipid.
13. The complex of claim 12, which is in the form of a liposome.
14. The complex of claim 12, wherein the free lipid is a phospholipid, a glycolipid, a cholesterol, a fatty acid or a derivative thereof.
15. The complex of claim 12, wherein a molar ratio of the GPIb:free lipid is 1:10–1:1000.
16. The complex of claim 12, wherein the complex is aggregatable in the presence of ristocetin.
17. The complex of claim 12, wherein the conjugate comprising GPIb and the lipid bonded via PAO is prepared, and then a complex of said conjugate and a free lipid is prepared.
18. A pharmaceutical composition comprising the complex of claim 12.
19. The pharmaceutical composition of claim 18, which is a platelet substitute.
20. The pharmaceutical composition of claim 18, which is an agent for the prophylaxis or treatment of a vascular disorder, a vascular damage or thrombosis.
21. A pharmaceutical agent for examination or diagnosis, which comprises, as an active ingredient, a labeling substance and the complex of claim 12.
22. The pharmaceutical agent of claim 21, wherein the labeling substance is a radioisotope, a paramagnetic metal for MRI, an iodide compound for X ray imaging, a fluorescent substance or a pigment.
23. A drug-containing composition comprising a drug and the complex of claim 12 as active ingredients.
24. The drug-containing composition of claim 23, wherein the drug is a hemostatic agent, a vasoconstrictor, an antiinflammatory agent, a thrombolytic agent, an anti-blood coagulator or an anti-platelet agent.

* * * * *

UNITED STATES PATENT AND TRADEMARK OFFICE
CERTIFICATE OF CORRECTION

PATENT NO.         : 6,926,884 B2
APPLICATION NO. : 10/220610
DATED                  : August 9, 2005
INVENTOR(S)        : Yasuo Ikeda et al.

Page 1 of 1

It is certified that error appears in the above-identified patent and that said Letters Patent is hereby corrected as shown below:

In the Title

On page 1 in item (54), Title:
Please replace "GPIB-LIPID BOND CONSTRUCT AND USE THEREOF" with --GPIb-LIPID CONJUGATE AND USE THEREOF--.

Signed and Sealed this

Nineteenth Day of September, 2006

JON W. DUDAS
*Director of the United States Patent and Trademark Office*